United States Patent
Thurwachter

(10) Patent No.: US 10,479,970 B2
(45) Date of Patent: Nov. 19, 2019

(54) CONTAINER WITH INSPECTION OPENING

(71) Applicant: Thurwachter GmbH & Co. KG, Sulzberg (DE)

(72) Inventor: Paul Thurwachter, Sulzberg (DE)

(73) Assignee: Thürwächter GmbH & Co. KG, Sulzberg (DE)

( * ) Notice: Subject to any disclaimer, the term of this patent is extended or adjusted under 35 U.S.C. 154(b) by 70 days.

(21) Appl. No.: 15/368,067

(22) Filed: Dec. 2, 2016

(65) Prior Publication Data

US 2017/0211024 A1    Jul. 27, 2017

(30) Foreign Application Priority Data

Dec. 3, 2015   (DE) .................. 10 2015 121 108

(51) Int. Cl.
| | |
|---|---|
| *B01F 7/00* | (2006.01) |
| *C12M 1/107* | (2006.01) |
| *B01F 15/00* | (2006.01) |
| *C12M 1/06* | (2006.01) |
| *C12M 1/00* | (2006.01) |

(52) U.S. Cl.
CPC ......... *C12M 21/04* (2013.01); *B01F 7/00733* (2013.01); *B01F 7/00741* (2013.01); *B01F 15/00694* (2013.01); *C12M 1/107* (2013.01); *C12M 23/36* (2013.01); *C12M 27/02* (2013.01); *C12M 21/00* (2013.01); *C12M 23/00* (2013.01)

(58) Field of Classification Search
CPC .............. B01F 7/00733; B01F 7/00741; B01F 15/00694; C02F 3/1284; C12M 21/04; C12M 27/02; C12M 27/06
USPC .......................................................... 366/331
See application file for complete search history.

(56) References Cited

U.S. PATENT DOCUMENTS

| | | | |
|---|---|---|---|
| 2012/0009664 A1* | 1/2012 | Buerger | C12M 21/04 435/286.5 |
| 2013/0170315 A1* | 7/2013 | Martens | B01F 7/00733 366/242 |

FOREIGN PATENT DOCUMENTS

| | | | |
|---|---|---|---|
| DE | 3345643 A1 | 6/1985 | |
| DE | 202004011561 U1 | 11/2004 | |
| DE | 102007012014 A1 | 9/2008 | |
| DE | 102009034127 A1 | 7/2010 | |
| DE | 102009041569 A1 | 4/2011 | |
| DE | 102012021206 A1 | 4/2014 | |
| EP | 1130084 A1 | 9/2001 | |
| WO | WO-9117818 A1 * | 11/1991 | .......... B01F 7/00741 |

* cited by examiner

*Primary Examiner* — Marc C Howell
(74) *Attorney, Agent, or Firm* — Loginov & Associates, PLLC; William A. Loginov

(57) ABSTRACT

The invention relates to a container, in particular a fermenter for a biogas plant, wherein in the container a mixer is arranged that can be removed through an inspection opening provided in a container wall. A boom is provided for this purpose. Furthermore, the invention relates to a related method and a related use.

13 Claims, 4 Drawing Sheets

CONTAINER WITH INSPECTION OPENING

BACKGROUND OF THE INVENTION

Figure 1:
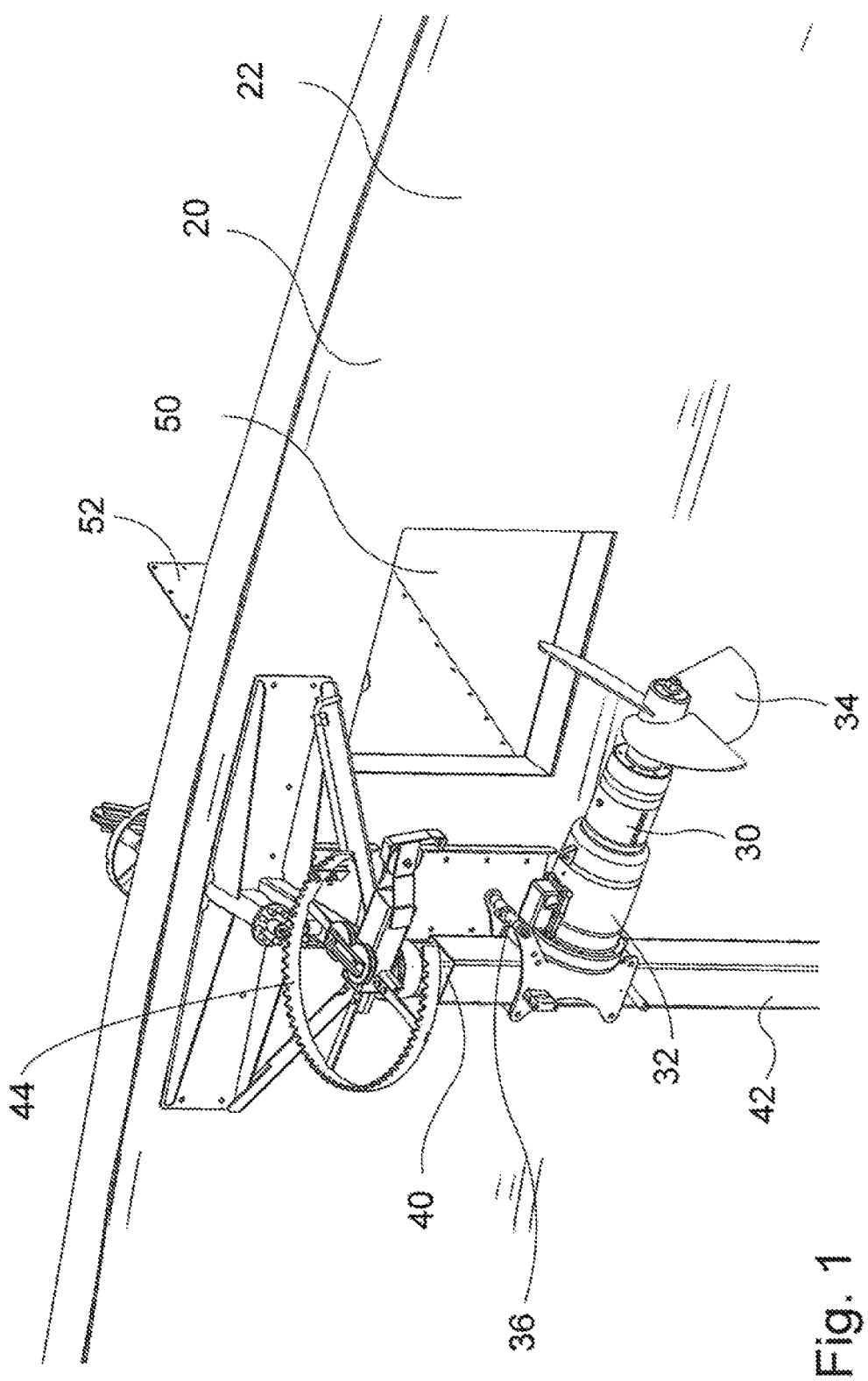

The invention relates to a container, a method for removing a mixer, and a use.

Containers are employed, for example, as fermenters for biogas plants or for storing or disintegrating manure. As a rule, containers of this kind are equipped with a mixer that takes care of mixing the biogas material or manure in the container. This improves, for example, an intended disintegration by bacteria and an also intended production of biogas, as inhomogenous parts in the material or manure are dissolved.

The problem when employing this kind of mixers is that they have to be removed on a regular basis for maintenance or when errors occur. As typically the containers referred to are sealed by a lid or cover on top in order to contain biogas and avoid excessive offensive smell this means a considerable effort with containers according to the state of the art. What is typically required is a difficult removal of the heavy lid, moving a crane above the container, attaching the mixer to the crane, and lifting the mixer out of the container from above by means of the crane.

In order to facilitate removal of the mixer, it has already been suggested to provide in a container wall an inspection opening which can be opened for removing the mixer. However, the effort for removing the mixer is very large even with such a modification as an external crane is required.

BRIEF SUMMARY OF THE INVENTION

Therefore it is an object of the invention to provide a container where the mixer can be removed easier. Further objects of the invention are to provide a related method and a related use.

This is solved, according to the invention, by a container, a method as well as a use according to the respective main claims. Advantageous modifications can be gathered, for example, from the respective sub-claims.

The invention refers to a container, in particular a fermenter for a biogas plant comprising a container wall laterally encircling the container. The container is provided with a mixer that has a motor and a joint propeller. This mixer offers in particular an advantageous mixing of biomass material or manure. The container is equipped with a mixer mount designed for carrying the mixer and moving it in different positions within the container.

Provision is made for a lockable inspection opening in the container wall through which the mixer can be removed. The mixer mount is configured for moving the mixer in a position horizontally next to the inspection opening.

Employing the container formed as described above makes laborious dismantling of a container lid, often required according to the state of the art, as well as moving a crane above the container obsolete. Instead the lateral inspection opening can be used what reduces the effort considerably.

According to the invention it is intended that on the outside or inside at the container wall, adjacent to the inspection opening a boom mounting for a boom is installed, wherein in the boom mounting a boom is fastened that is provided with a crossbeam extending at least partly across the inspection opening. The boom can swing around a vertical axis.

The modification according to the invention facilitates removal of the mixer as no external crane or other external lifting devices are required. The container already has an attached boom adapted for removing the mixer easily and with little effort for possible servicing. This reduces the need of other equipment—in particular heavy equipment such as a crane—that have to be supplied for such a servicing.

The boom can swivel around a vertical axis, and thus the mixer can be swung out of the container. This makes removal of the mixer particularly simple, as the swiveling motion is simple.

Preferably, the mixer mount is formed such that the mixer can be removed adjacent to the inspection opening from the mixer mount. This facilitates removal of the mixer. For example, an easy to open locking mechanism may be provided.

In particular, the mixer mount can be configured as vertical mast and the mixer travels along it. A mast of this kind may be configured, for example, even transversely.

Preferably, the mixer mount is configured for swinging the mixer around a vertical axis or an axis of the mast. In an advantageous way it can be set here in which direction mixing is carried out, for example in order to dissolve selected solidified areas.

According to a preferred embodiment the boom carries a lifting device, in particular a horizontal crossbeam extending partly in the container for attaching the mixer in the container through the opened inspection opening. This facilitates attaching the mixer. It is clear that this situation occurs in particular during removal or putting back of the mixer.

Advantageously, the lifting device can swivel around a horizontal axis. Thus it can be balanced, for example, in the way described below. Furthermore, it can swivel in particular also in a preferably horizontal plane.

According to a development the horizontal crossbeam can be linked on one of its ends to the mixer, and on an opposite end with a counter weight, so that the horizontal crossbeam is balanced at least essentially. This facilitates handling.

Preferably, the counter weight can be a container filled or fillable with ballast, in particular water. This allows adjustment to the weight of the mixer.

Preferably, the mixer can be attached to the mixer mount by means of a stop pin adjacent to the inspection opening. Thus it can be fixed for removal.

Furthermore, the invention relates to a method for the removal of a mixer from a container laterally encircled by a container wall, in particular a fermenter, in particular for a biogas plant, wherein the method comprises following steps:

Moving the mixer horizontally next to an inspection opening in the container wall, Opening the inspection opening, Attaching the mixer to a lifting device attached to a boom, wherein the boom is fastened to a boom mounting arranged outside or inside at the container wall adjacent to the inspection opening, comprising an at least partly over the inspection opening extending crossbeam, and swiveling around a vertical axis, and Removing the mixer from the container by means of the lifting device.

The method according to the invention facilitates that a mixer can be removed easily from the side, wherein removing a container lid and employing an extern crane—necessary as a rule according to the state of the art—is expendable. Concerning other advantages it is referred to the above description of the container according to the invention.

In particular, a container can be employed that is designed according to the invention. Regarding the container, in this case all described modifications and embodiments can be used.

In particular, the mixer can be moved next to the inspection opening by means of a mixer mount located in the container. This allows easy attachment to a device for removing the mixer.

Prior to the step of attaching to a lifting device the mixer can be swung around a vertical axis. This allows moving the mixer in a position where it can be removed easier.

Preferably, the method comprises a step for attaching a counter weight to one end of a horizontal crossbeam of the lifting device. Thus the horizontal crossbeam can be balanced advantageously.

Conveniently, the mixer can be removed by swiveling the boom around the vertical axis. This motion is easy to realize.

Advantageously, the lifting device can be configured as horizontal crossbeam. This facilitates the procedure already described above.

According to a preferred embodiment the lifting device is fastened to the crossbeam. Thus a movement of the lifting device can be derived advantageously from the movement of the boom.

Preferably, the mixer is fastened removably to a mixer mount in the container, and is taken off the mixer mount prior to removal. The mixer mount can show in particular the above-mentioned functions.

Furthermore, the invention relates to a use of an inspection opening that is formed in a sidewall of a container, in particular a fermenter, in particular for a biogas plant, for removing a mixer located in the container, and this is by using a boom, wherein the boom is attached to a boom mounting provided outside or inside at the container wall adjacent to the inspection opening, is provided with a crossbeam extending at least partly across the inspection opening, and can swing around a vertical axis.

Regarding the related advantages it is referred to the above description.

In particular, the container can be configured according to the invention. Concerning a container according to the invention all described embodiments and modifications may be used.

Conveniently removal is carried out in horizontal direction. As a simple embodiment this has proven successful.

Removal can be done particularly advantageously according to a method of the invention. All described embodiments and modifications can be used.

In this context it is pointed out in particular that all characteristics and features described with relation to the device but also all methods can accordingly be translated to the formulation of the method according to the invention, and are considered as applicable and thus also disclosed according to the invention. The same goes vice versa, this means constructive, that is device characteristics only referred to with regard to the method can also be considered and claimed in the frame of the device claims, and are also considered disclosed.

SHORT DESCRIPTION OF THE DIFFERENT VIEWS OF THE DRAWING

In the drawing the invention is shown schematically in particular in an example. In the figures:

FIG. 1 a perspective view of a part of a container according to the invention with mixer and inspection opening.

Figure 2:
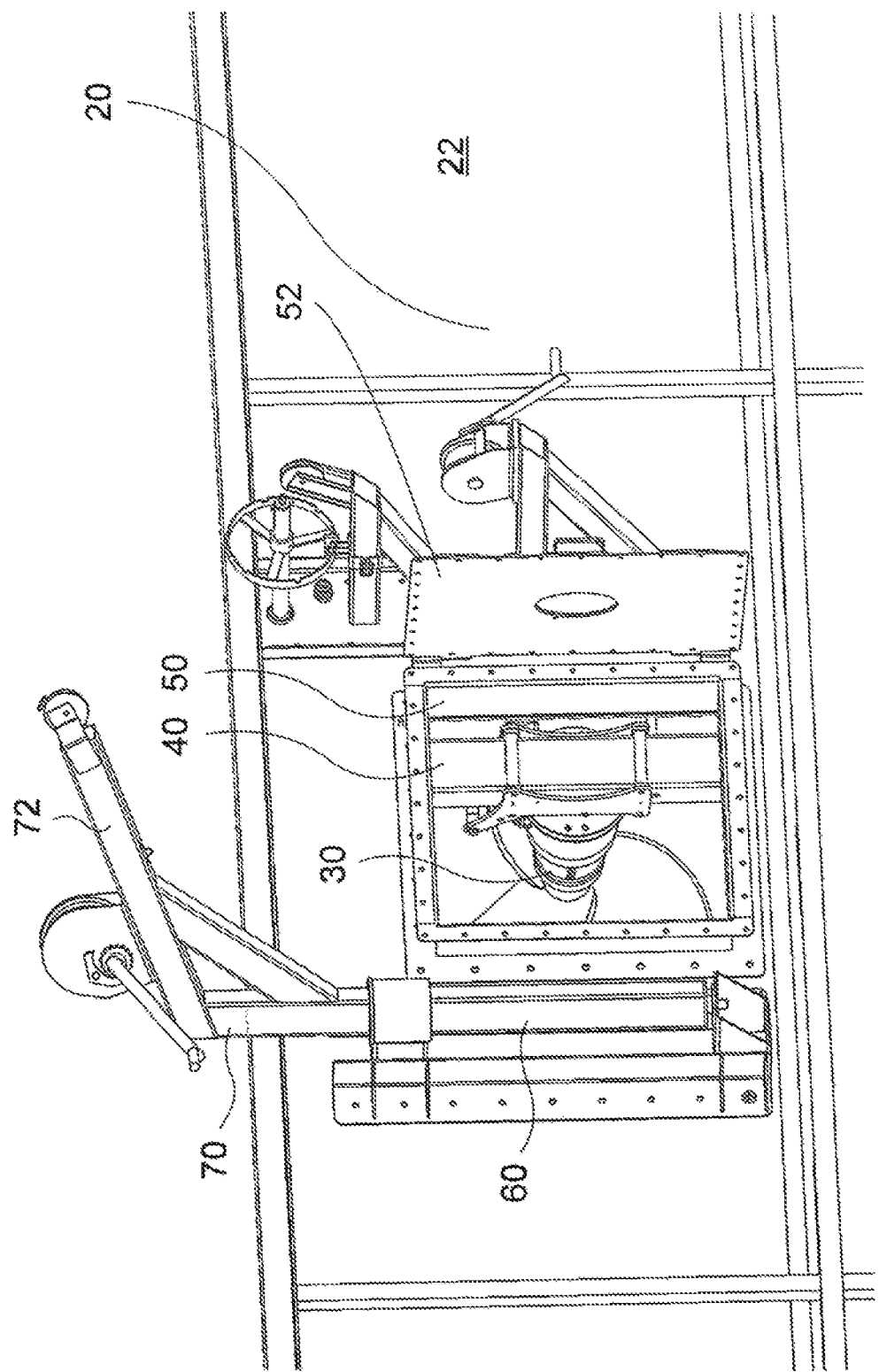

FIG. 2 an exterior view of the container according to the invention.

Figure 3:
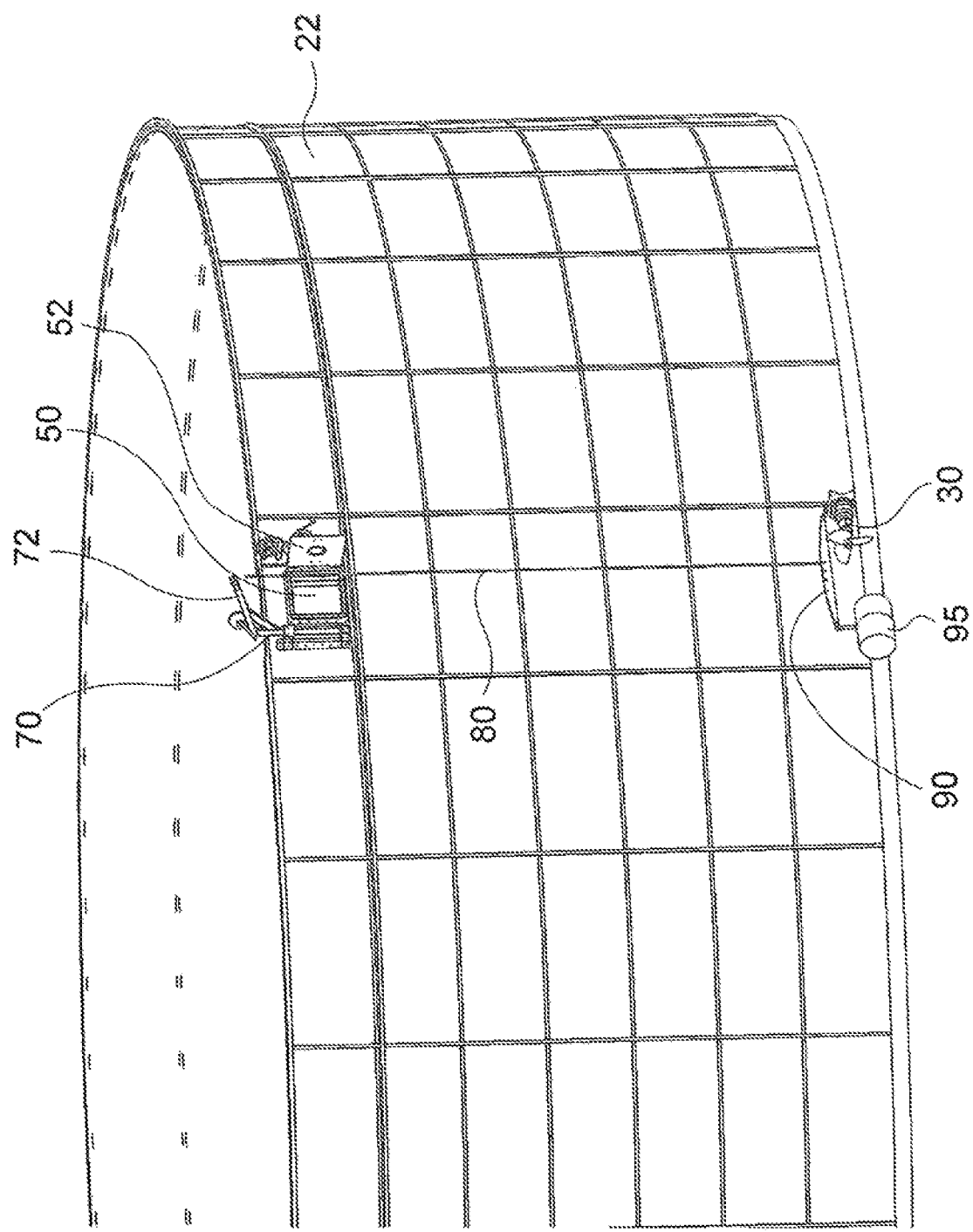

FIG. 3 another exterior view of the container according to the invention.

Figure 4:
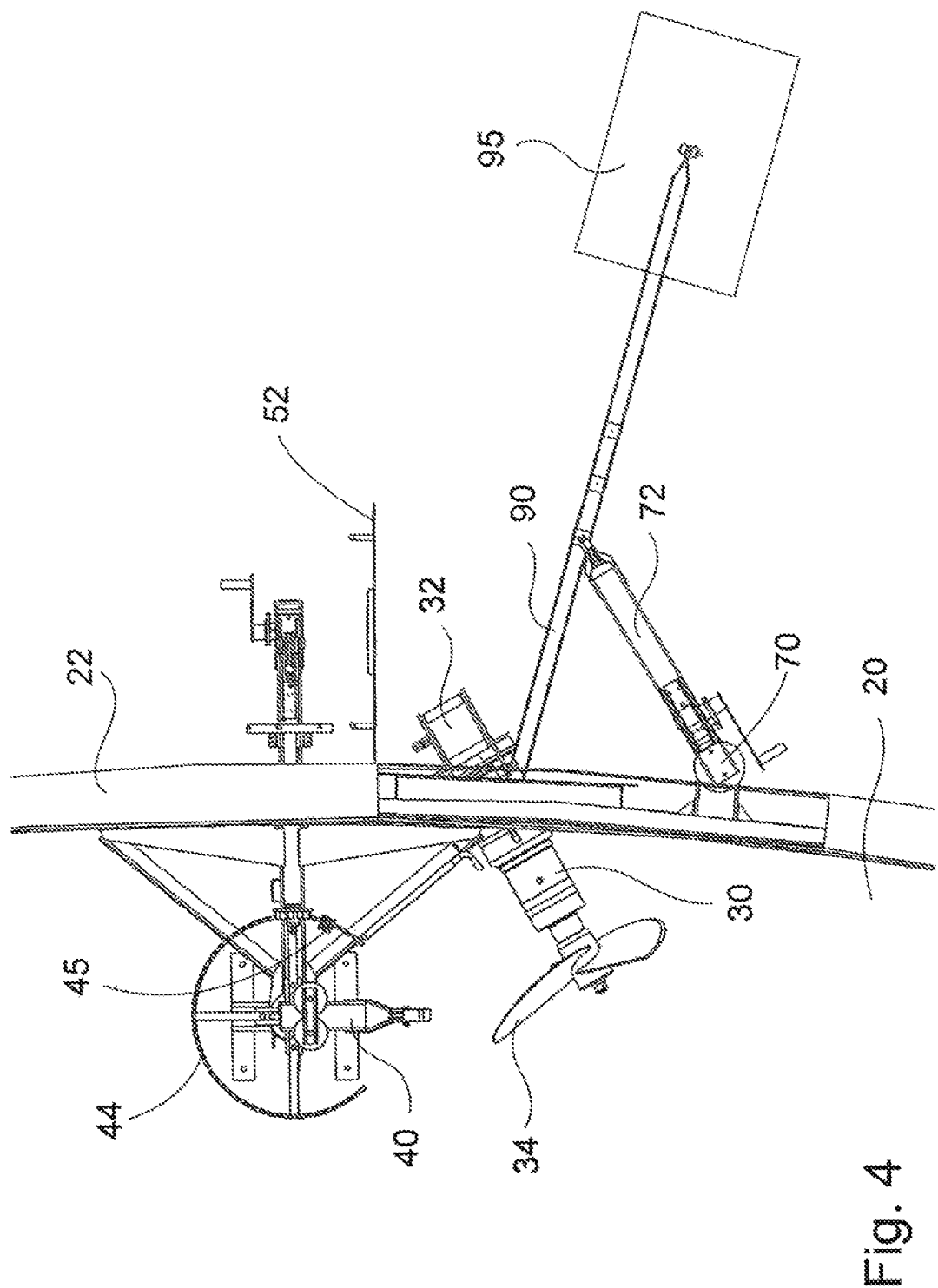

FIG. 4 a plan view of the container according to the invention.

DETAILED DESCRIPTION OF THE PREFERRED EMBODIMENT

Identical or corresponding elements in the figures each are referred to by identical reference numbers, and therefore are, if not useful, not described anew. Disclosures contained in the entire description can accordingly be translated to identical parts with identical reference numbers or identical component designations. Also position specifications chosen in the description such as, for example, above, below, laterally etc. refer to the directly described or shown figure, and have to be translated accordingly to the new position when changing the position. Furthermore also single characteristics or combinations of characteristics from the different shown and described embodiments can be independent, inventive solutions or solutions according to the invention.

FIG. 1 shows a part of a container 20 designed according to an embodiment of the invention. The container 20 is preferably in particular a fermenter for a biogas plant. It has a roof in order to retain produced biogas and to lead it to its purpose, however, this is not shown in the figures.

Container 20 has a container wall 22.

In the interior of the container 20 there is a mixer 30. Mixer is formed by a motor 32 and a propeller 34. It serves for mixing biomass in the container 20 and thus provides an improvement in producing biogas. Solidified areas e. g. can be dissolved.

Mixer 30 is attached to a mixer mount 40, and the mixer mount 40 is attached to the container wall 20. The mixer mount 40 is configured essentially as vertical mast 42. The mixer is vertically mounted to the mast 42 moving on a slide; this facilitates the use of the mixing effect of the mixer 30 on different levels in container 20.

As shown, mast 42 is designed swiveling around its vertical axis; this makes it possible to set the direction in which the mixing effect is to be executed. A driven sprocket 44 is provided hereto.

In the container wall 22 a lateral inspection opening 50 is provided. The purpose for this is removal of the mixer 30 for maintenance. In particular the following procedure or method can be employed. The inspection opening 50 can be sealed by means of a flap 52 so that during the regular operation biogas is prevented from escaping laterally.

Mixer 30 can be moved along mast 42 in a position where the mixer 30 is immediately neighboring the inspection opening 50. This corresponds with the situation shown in FIG. 1. The mixer can be fixed in this situation by means of a stop pin 36.

FIG. 2 shows an exterior view of container 20. Mixer 30 and mixer mount 40 are partly visible through the opened inspection opening 50.

To the outside of the container wall 20 a boom mounting 60 is attached. A boom 70 is attached thereto, and at its upper side a crossbeam 72 is provided. Boom 70 can swivel around a vertical axis which is also defined by the boom mounting 60. Advantageously this can be used for removing mixer 30 from container 20.

FIG. 3 shows an exterior view to container 20 after removing mixer 30. Mixer 30 is suspended on a horizontal crossbeam 90. The horizontal crossbeam 90 is attached to a rope 80, while rope 80 dangles from crossbeam 72 of boom 70.

The horizontal crossbeam 90 can swivel around a horizontal axis defined by the suspension point on the rope 80. As shown mixer is arranged spaced apart from this suspension point. For keeping the horizontal crossbeam 90 balanced, opposite the mixer a counter weight 95 is arranged. This has the shape of a tank, and can be filled with water as ballast material, and, in this case, is filled. Just enough water has been filled in the counter weight 95 so that the horizontal crossbeam 90 is balanced.

FIG. 4 shows a situation prior to removal of the mixer 30 from the container 20. The mixer 30 is attached to the horizontal crossbeam 90. Additionally, the counter weight 95 is attached opposite to the horizontal crossbeam 95. This facilitates the following procedure:

Counter weight 95 is filled with water until the horizontal crossbeam 90 is in a torque-free condition. This can be determined, for example, by measuring forces or monitoring. After that the mixer can be taken off the mixer mount 40. Then boom 70 can be swilled outwards around its vertical turning axis so that the mixer 30 is removed from the container 20. Then flap 52 can be closed.

After that the horizontal crossbeam 90 can be lowered for example such that the situation shown in FIG. 3 may be reached.

It is clear that at the sprocket 44, in particular during routine operation, this is when the mixer 30 is used normally, a bracket-like stopper 45 may be attached preventing the mixer 30 from being moved too close to the container wall 22. Advantageously a release bolt may be provided facilitating the further movement for removal of the mixer. In FIG. 4 the stopper 45 is arranged in a position not corresponding with the routine operation but serving for removing the mixer.

In the following possible characteristics of the suggestion are shown in a structured way. The following characteristics, shown in a structured way, may combined with each other in any way, and can be included in any combination in the claims of the application. It is clear for a person skilled in the art that the invention already results from the subject matter with the least characteristics. In the following in particular advantageous or possible embodiments, however not the only possible embodiments of the invention are shown.

The invention comprises:

A container, in particular fermenter for a biogas plant comprising a container wall that encircles the container laterally; and the container is provided with a mixer comprising a motor and a joint propeller; and the fermenter is provided with a mixer mount designed for carrying the mixer and moving it to different positions within the container, wherein in the container wall a sealable inspection opening is provided through which the mixer can be removed; and the mixer mount is designed such that it moves the mixer in a position horizontally next to the inspection opening.

The above-mentioned container, wherein the mixer mount is designed such that the mixer adjacent to the inspection opening can be removed from the mixer mount.

The above-mentioned container, wherein the mixer mount is designed as vertical mast, and the mixer can travel along it.

The above-mentioned container, wherein the mixer mount is designed such that it swivels the mixer around a vertical axis.

The above-mentioned container, wherein on the outside or inside of the container wall, adjacent to the inspection opening a boom mounting for a boom is arranged.

The above-mentioned container, wherein in the boom mounting a boom is installed that is provided with a crossbeam at least partly extending over the inspection opening.

The above-mentioned container, wherein the boom can swivel around a vertical axis.

The above-mentioned container, wherein the boom carries a lifting device, in particular a horizontal crossbeam projecting partly through the open inspection opening in the container for attaching the mixer located in the container.

The above-mentioned container, wherein the lifting device can swing around a horizontal axis and/or in a horizontal plane.

The above-mentioned container, wherein the horizontal crossbeam can be connected on one of its ends with the mixer and on another, opposite end with a counter weight, so that the horizontal crossbeam is at least essentially balanced.

The above-mentioned container, wherein the counter weight is a container that can be filled or is filled with ballast material, in particular water.

The above-mentioned container, wherein the mixer can be attached to the mixer mount adjacent to the inspection opening by means of a stopper bolt.

A method for removing a mixer from a container, in particular a fermenter, in particular for a biogas plant, encircled by a container wall, and in particular according to the invention, wherein the method comprises the following steps:

Moving the mixer horizontally next to an inspection opening in the container wall, Opening of the inspection opening, Attaching the mixer to a lifting device, and Removing the mixer from the container by means of the lifting device.

The above-mentioned method, wherein the lifting device is attached to a boom, wherein the boom is attached to a boom mounting provided outside or inside at the container wall adjacent to the inspection opening, is provided with a crossbeam extending at least partly over the inspection opening, and swivels around a vertical axis.

The above-mentioned method, wherein the mixer is moved next to the inspection opening by means of a mixer mount located in the container.

The above-mentioned method, wherein the mixer is swung around a vertical axis prior to the step of attaching to a lifting device.

The above-mentioned method, wherein the method comprises a step of attaching a counter weight to one end of a horizontal crossbeam of the lifting device.

The above-mentioned method, wherein the mixer is removed by swiveling the boom around the vertical axis.

The above-mentioned method, wherein the lifting device is designed as horizontal crossbeam.

The above-mentioned method, wherein the lifting device is attached to the crossbeam.

The above-mentioned method, wherein in the container the mixer is attached releasably to a mixer mount, and is taken off the mixer mount prior to removal.

A use of an inspection opening, that is located in a sidewall of a container, in particular fermenter, in particular for a biogas plant and in particular according to the invention, for removing a mixer located in the container.

The above-mentioned use carried out by employing a boom, wherein the boom is attached to a boom mounting that is provided on the outside or inside at the container wall adjacent to the inspection opening, has a crossbeam extending at least partly over the inspection opening, and can swivel around a vertical axis.

The above-mentioned use, wherein removal is carried out in horizontal direction.

The above-mentioned use, wherein removal is carried out by means of a method according to the invention.

The claims filed with the application now and to be filed later on are without prejudice for obtaining a broader protection.

If here, on closer examination, in particular of the relevant state of the art, it turns out, that one or the other characteristics may be convenient for the objective of the invention, however not decisively important, of course, already now a formulation is aimed at which does not contain anymore such a characteristic, in particular in the main claim. Also a sub-combination is covered by the disclosure of this application.

Furthermore it has to be observed that the embodiments and modifications of the invention described in the different examples and shown in the figures can be combined with each other in any way. Here single or several characteristics can be exchanged at will. These combinations of characteristics are also disclosed.

The references in the sub-claims relate to the further design of the subject matter of the main claim through the characteristics of the respective sub-claim. These are, however, not to be understood as a waiver of independent subjective protection of the matter for the characteristics of the referred sub-claims.

Characteristics only disclosed in the description or even single characteristics from claims comprising a number of characteristics may be taken over in the independent claim/claims at any time as being of inventive relevance to distinguish from the state of the art, and this is even if such characteristics have been mentioned in the context with other characteristics or achieve particularly convenient results in connection with other characteristics.

Although the invention has been described in terms of specific embodiments which are set forth in considerable detail, it should be understood that this is by way of illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

The invention claimed is:

1. A container with a container wall laterally encircling the container, comprising:
   a mixer provided with a motor and a joint propeller, the container being provided with a mixer mount configured for carrying the mixer and moving it in different positions within the container, wherein, in the container wall, a sealable inspection opening is formed, through which the mixer can be removed, and the mixer mount is configured for moving the mixer in a position horizontally next to the inspection opening, wherein, either outside or inside to the container wall adjacent to the inspection opening, a boom mounting for a boom is attached, and wherein, in the boom mounting, a boom is installed that has a crossbeam extending at least partly over the inspection opening, and wherein the boom is arranged to swing around a vertical axis.

2. The container according to claim 1, wherein the mixer mount is formed such that the mixer adjacent to the inspection opening is removable from the mixer mount.

3. The container according to claim 1, wherein the mixer mount is formed as a vertical or a transverse mast and the mixer travels along it.

4. The container according to claim 1, wherein the boom carries a lifting device extending partly in the container through the open inspection opening for attaching the mixer located in the container.

5. The container according to claim 4, wherein the lifting device is a horizontal crossbeam connectable on one of its ends with the mixer and on an opposite one of the ends with a counter weight, so that the horizontal crossbeam is balanced.

6. The container according to claim 5, wherein the counter weight is a container filled or fillable with ballast.

7. A method for removing a mixer from a container laterally encircled by a container wall, wherein the method comprises the following steps:
   moving the mixer horizontally next to an inspection opening in the container wall;
   opening the inspection opening;
   attaching the mixer to a lifting device that is attached to a boom, wherein the boom is installed in a boom mounting attached either outside or inside to the container wall adjacent to the inspection opening, has a crossbeam extending at least partly over the inspection opening, and being arranged to swing around a vertical axis; and
   removing the mixer from the container by means of the lifting device.

8. The method according to claim 7, wherein the step of removing the mixer includes swinging the boom around the vertical axis.

9. The method according to claim 7, wherein the lifting device is formed as horizontal crossbeam.

10. The method according to claim 7, wherein the lifting device is attached to the crossbeam.

11. The method according to claim 7, wherein the mixer is attached removably to a mixer mount in the container, and is taken off the mixer mount before removal.

12. A method for using an inspection opening formed in a lateral container wall of a container for removal of a mixer located in the container comprising the steps of:
   providing a boom, wherein the boom is installed in a boom mounting provided either outside or inside at the container wall adjacent to the inspection opening, and has a crossbeam extending at least partly over the inspection opening; and
   swinging the boom around a vertical axis to remove the mixer.

13. The method according to claim 12, wherein the removal of the mixer is carried out in horizontal direction.

* * * * *